United States Patent [19]

Pugh et al.

[11] Patent Number: 4,515,333

[45] Date of Patent: May 7, 1985

[54] ADJUSTABLE SUPPORT FOR AN OPTICAL OR OTHER INSTRUMENT

[75] Inventors: Stuart Pugh; Douglas G. Smith, both of Loughborough, England; Chee M. Lee, Jurong Town, Singapore; Leslie R. Parr, Leicester; John N. Birkett, Aylesbury, both of England; Richard G. Stibbs, Glasgow, Scotland; Tet C. Tai, Petaling Jaya Selangor, Malaysia

[73] Assignee: University of Technology, Leicestershire, England

[21] Appl. No.: 333,870

[22] PCT Filed: Apr. 14, 1981

[86] PCT No.: PCT/GB81/00068

§ 371 Date: Dec. 14, 1981

§ 102(e) Date: Dec. 14, 1981

[87] PCT Pub. No.: WO81/03054

PCT Pub. Date: Oct. 29, 1981

[30] Foreign Application Priority Data

Apr. 15, 1980 [GB] United Kingdom ............. 8012388

[51] Int. Cl.³ ............................................. F16L 3/00
[52] U.S. Cl. ............................. 248/122; 248/123.1; 248/124
[58] Field of Search ........... 248/122, 123.1, 124, 248/125, 127, 162.1, 132, 289.1, 282; 350/513, 514, 515, 522, 521

[56] References Cited

U.S. PATENT DOCUMENTS

| 2,602,863 | 7/1952 | Raymond et al. | 248/122 |
| 2,967,458 | 1/1961 | Stone | 350/514 |
| 3,776,614 | 12/1973 | Kloots et al. | 350/514 |
| 3,971,538 | 7/1976 | Marvich | 248/122 |
| 4,157,859 | 6/1979 | Terry | 350/514 |
| 4,166,602 | 9/1979 | Nilsen et al. | 248/123.1 |
| 4,344,595 | 8/1982 | Heller et al. | 248/123.1 |

FOREIGN PATENT DOCUMENTS 2242266 8/1972 Fed. Rep. of Germany.
2320266 5/1973 Fed. Rep. of Germany.

Primary Examiner—William H. Schultz
Assistant Examiner—Ramon O. Ramirez
Attorney, Agent, or Firm—D. N. Halgren; V. A. White

[57] ABSTRACT

An adjustable support for an optical or other instrument (e.g. a binocular microscope for use by a surgeon in neurosurgery) which readily permits adjustment in the position of the instrument in a predetermined spatial envelope and/or adjustment of the orientation of the instrument at any given position within that envelope, and which is compact, relatively inexpensive to manufacture, easy to adjust, and incorporates a high degree of safety, comprises a rod-like carrier, supporting the instrument at one end and an adjustable counterweight at the other, mounted, by a ball joint arrangement on a linkage system rotatably supported on a column. The ball joint arrangement and the other joint arrangements in the linkage system are provided with clamping devices, normally urged to clamping position by springs but released by the application of air pressure under control of a switch device.

11 Claims, 12 Drawing Figures

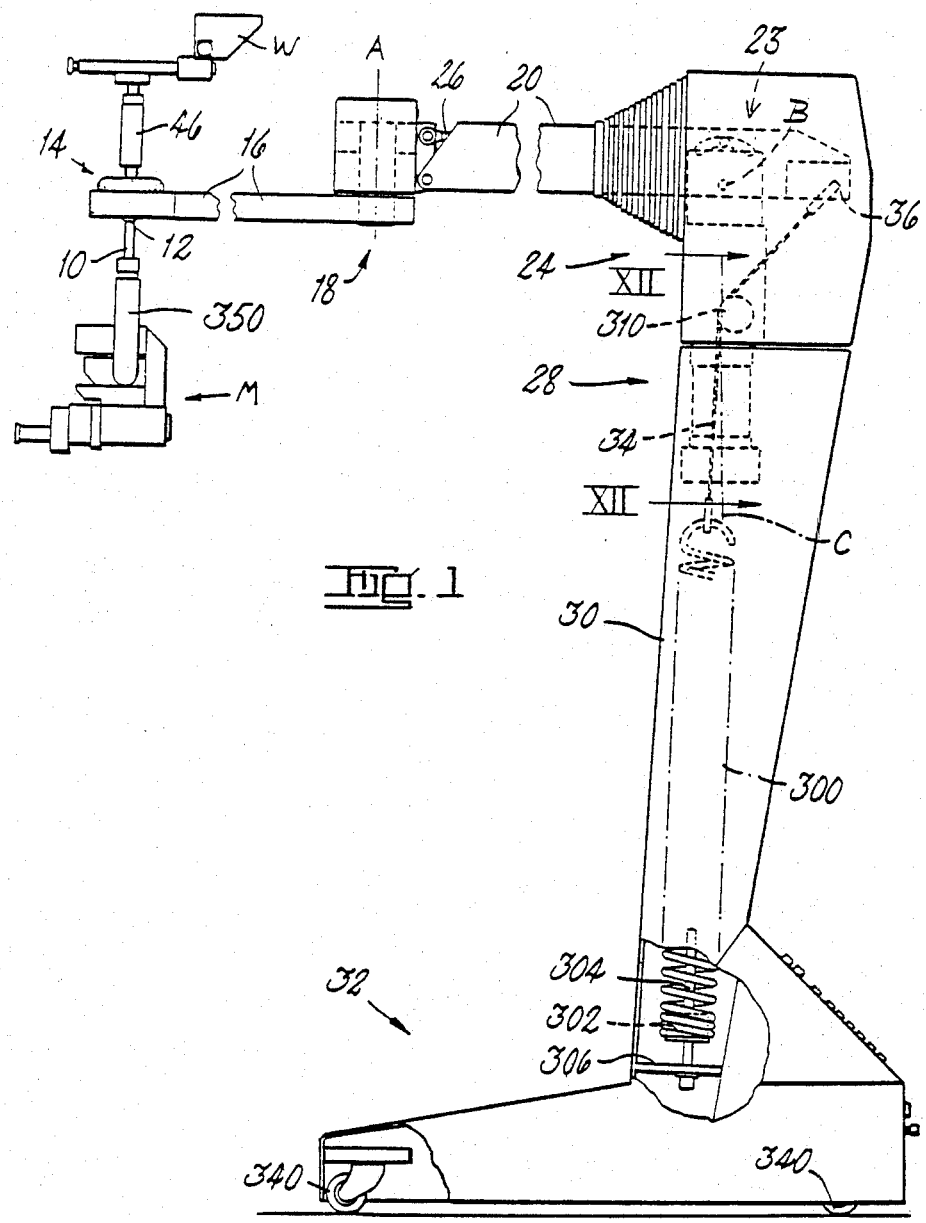

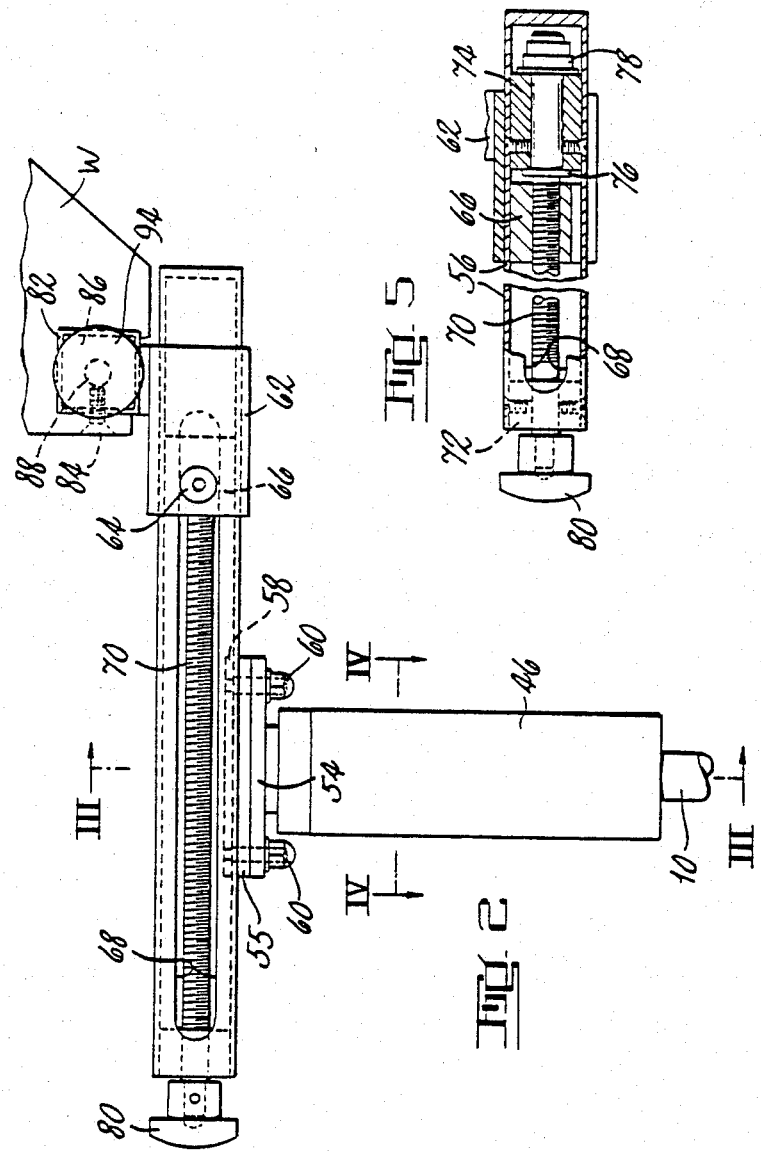

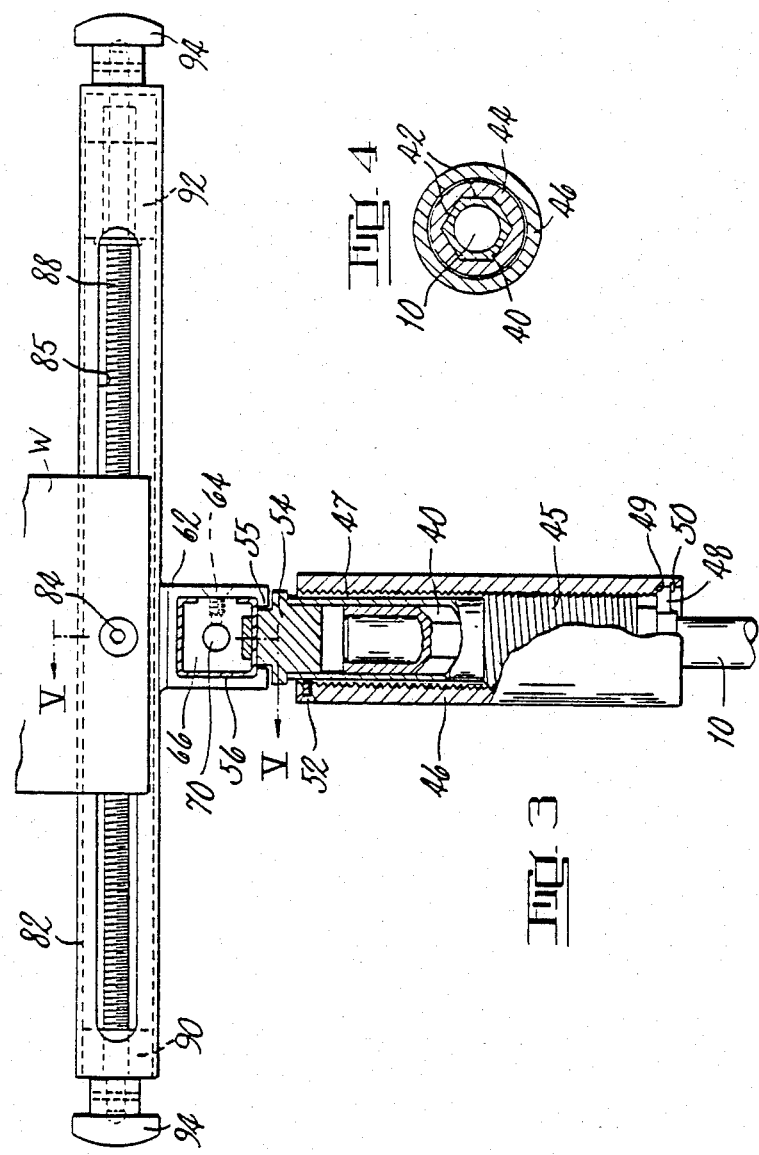

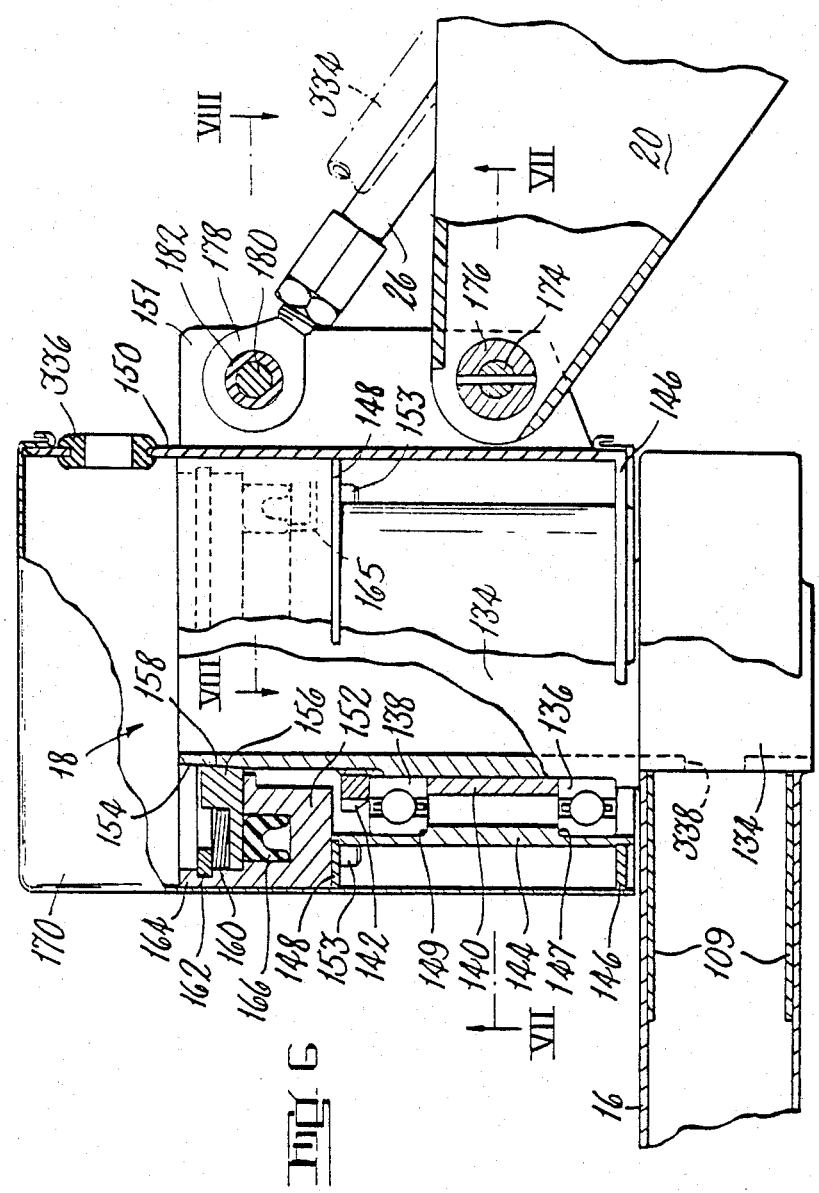

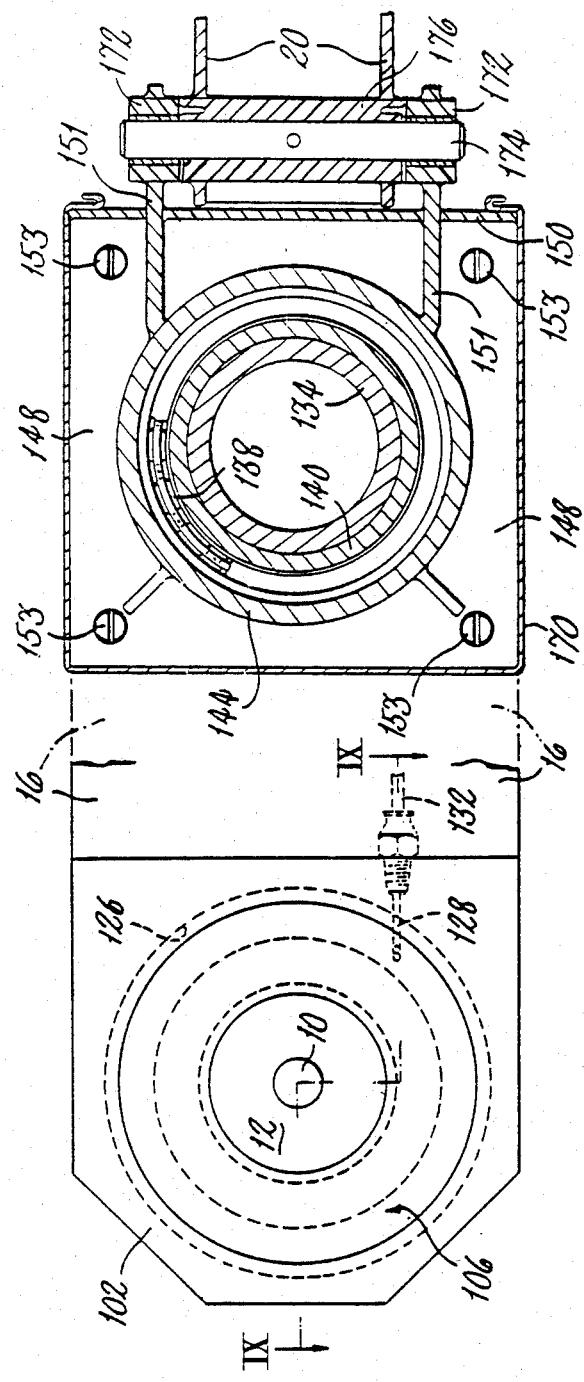

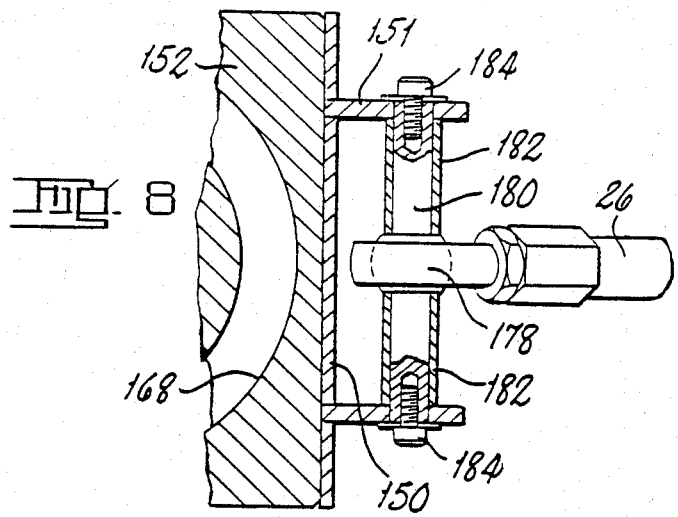
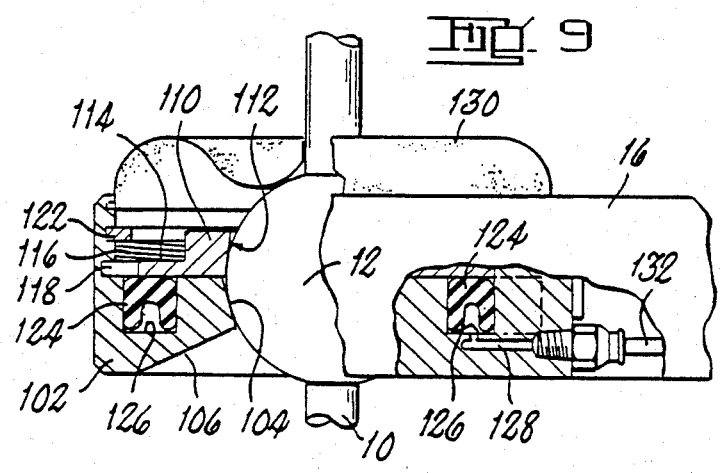

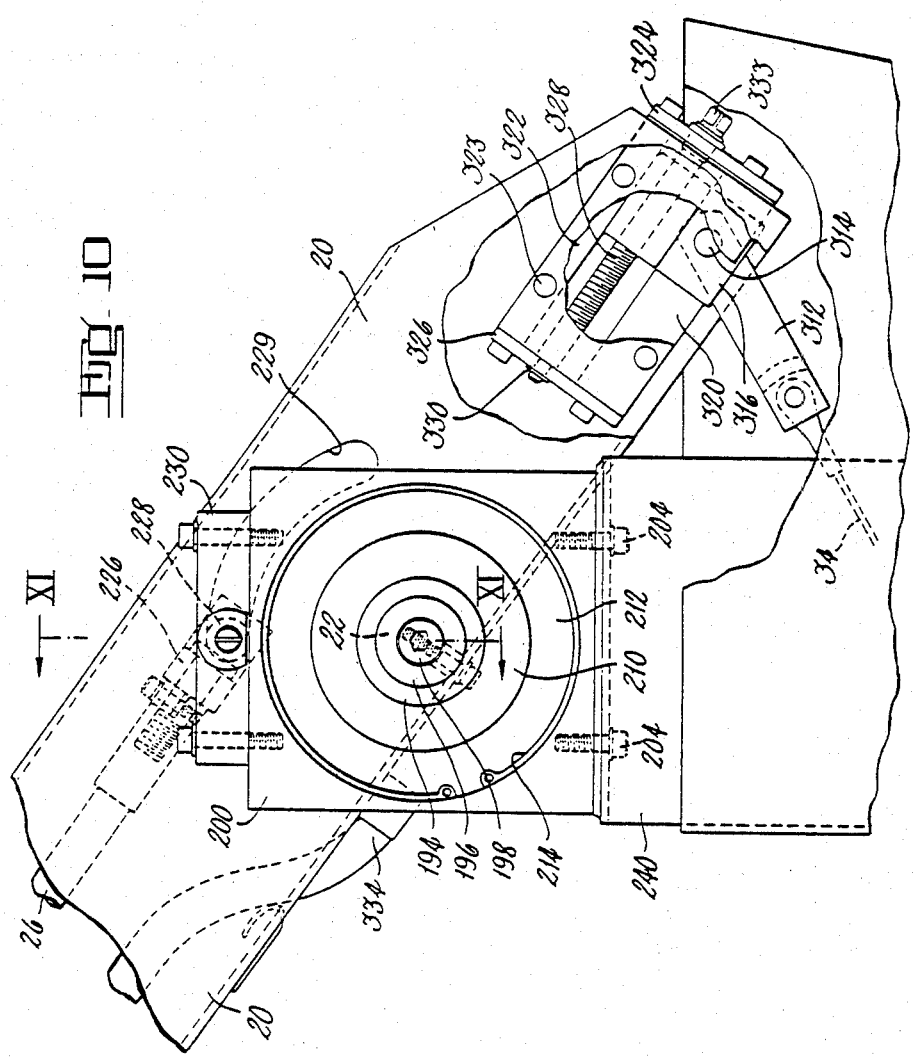

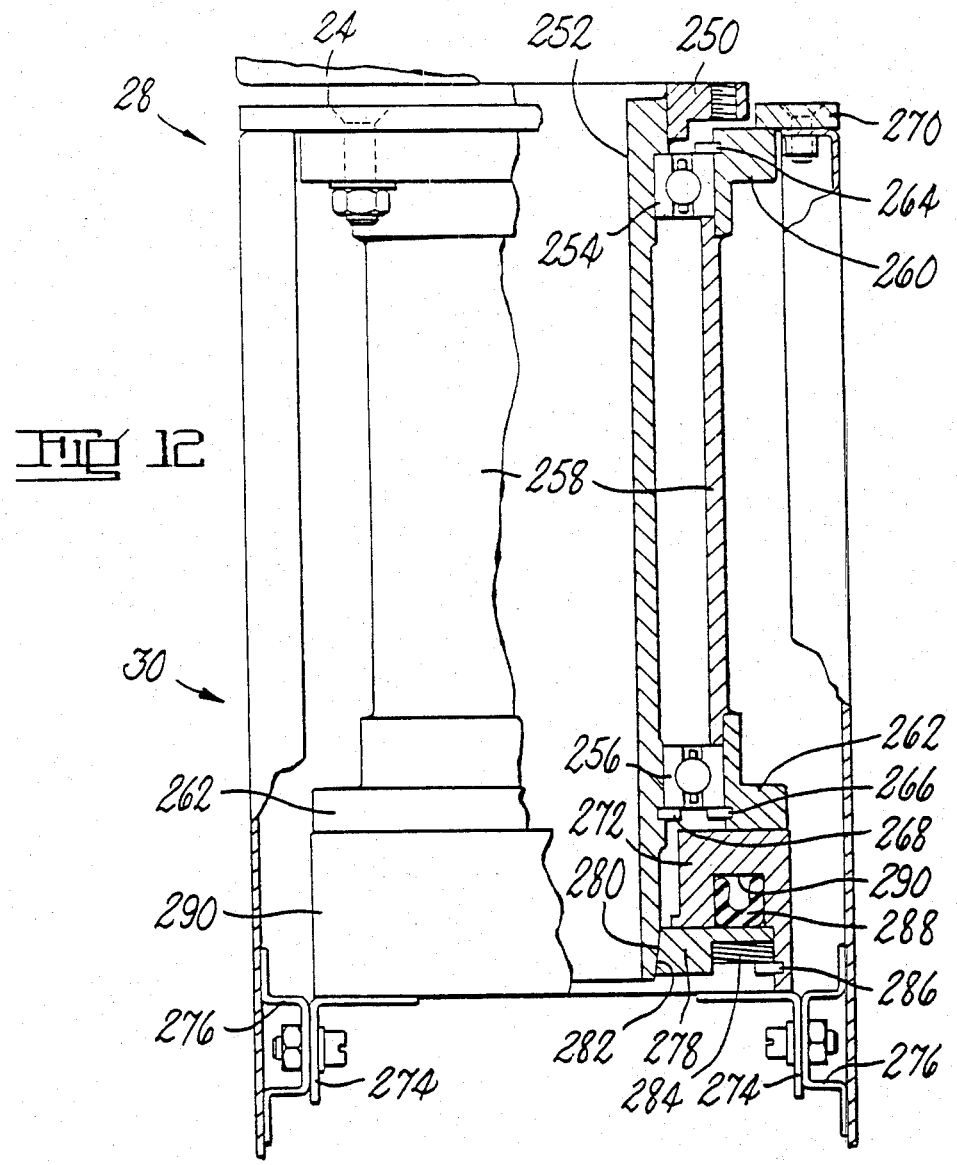

ADJUSTABLE SUPPORT FOR AN OPTICAL OR OTHER INSTRUMENT

TECHNICAL FIELD

The present invention is concerned with an adjustable support for an optical or other instrument. More particularly, the invention is concerned with an adjustable support which readily permits adjustment in the position of the instrument in a predetermined spatial envelope and/or adjustment of the orientation of the instrument at any given position within that envelope, the support having associated with it clamping means for maintaining the instrument in the desired position and/or orientation, the clamping means being readily operated by a person using the instrument. One field of application of a support in accordance with the present invention is in the supporting of an optical instrument such as a binocular microscope, camera, television camera or the like during delicate surgical operations, e.g. neuro-surgical operations. During such operations a binocular microscope may often be used in conjunction with a television camera for continuous monitoring of the operation by a surgeon, and a cine or still camera may also be used for recording certain stages of the operation for use in training medical staff.

BACKGROUND ART

With a view to meeting the requirements of surgeons, a number of supports, some floor mounted some ceiling mounted, have been proposed. Whilst the use of microscopes and related optical instruments has enabled surgeons to achieve impressive results, existing supports still have some drawbacks. It will be understood that the very restricted field of view when using a microscope at high magnification necessitates its frequent movement as an operation progresses. In some cases, using existing equipment, these movements are relatively difficult to achieve and the time in making the necessary adjustments may account for as much as 40 percent of the operating time. This is not only tiring for the surgeon but greatly increases the chance of complications for the patient. Therefore a need exists for a support whereby manipulating the microscope (or other optical instrument) requires very little effort on the part of the surgeon, but which is capable of sustaining the instrument in the required position without the surgeon having to remove his hands from the operating area to effect unclamping, adjustment, and reclamping of the apparatus.

While a number of known supports employ a combination of pivotal movements and linear (e.g. sliding) movements of components parts to provide for the desired spatial envelope of displacements of an optical instrument, it has been observed that, for the smoothest operation, a system employing only pivotal movements of component parts of the support is preferred. One such support is disclosed in UK Patent Specification No. 1357261. In the support disclosed in that specification a carrier for an optical observation device such as a binocular microscope is fixed onto an end member of a linkage rotatably mounted on a socket by means of a column, the said end member being spatially freely movable as a result of the combination of rotary movements possible about at least three axes. Furthermore, in the support disclosed in said specification, the orientation of the optical axis of the observation device may be adjusted by means of a triple axis fully universal linkage which enables freely combinable rotation thereof in three mutually perpendicular and intersecting directions by a handgrip, this linkage being effective to fix the carrier on the end member of the linkage referred to in the previous sentence. In the support disclosed in said specification a number of blocking devices are provided for clamping the carrier for the optical observation device in its desired spatial position and/or orientation, there being three of these blocking devices associated with bearings of the triple axis fully universal linkage and three more associated with bearings of the linkage rotatably mounted on said socket. The blocking devices are of the electromagnetic type, being rendered operative by the passage of electric current through coils of the blocking devices. When the surgeon wishes to adjust the position and/or orientation of the optical instrument supported on the support disclosed in said specification he actuates a switch mounted on a handgrip associated with the carrier for the instrument to effect either a complete de-energisation of the electromagnetic coils of the blocking devices or an intermittent de-energisation thereof. Counterbalancing means, comprising a weight adjustably mounted on an extension of one of the links of the linkage rotatably mounted on said socket, is provided to counterbalance gravity-produced turning moments of the entire stand in respect of the rotation axis of a parallelogram linkage to a column which is rotatable about said socket. Furthermore, by adjustment of the optical instrument on its carrier, compensation of gravity-produced turning moments of the triple axis fully universal linkage and of the optical instrument about the common intersection point of the three rotation axes is possible. These counterbalancing facilities seek to avoid unwanted movements of the optical instrument when the blocking devices are released.

While a support as disclosed in said specification goes some way to meeting the requirements of surgeons employing optical instruments such as a binocular microscope to assist them during delicate operations we have found it possible to effect further improvements in a number of respects.

The triple axis fully universal linkage of the support disclosed in said specification is a complex arrangement requiring many parts and a total of three blocking devices associated one with each of the pivots providing for rotation about said three axes. It occupies a considerable amount of space in the vicinity of the observation point and counterbalancing adjustments necessitate adjustment of the position of the optical instrument itself on its carrier. Furthermore, in the event of failure of the electrical supply, the blocking devices are unclamped permitting undesired free movement of the optical instrument.

Various objects of the invention are to overcome, or minimise, these disadvantages and provide an improved support which is compact, relatively inexpensive to manufacture, easy to adjust, and incorporate a high degree of safety in use.

DISCLOSURE OF INVENTION

The invention provides an adjustable support for an optical or other instrument, which support permits adjustment of the position of the instrument in a predetermined spatial envelope and/or adjustment of the orientation of the instrument at any given position within that envelope, said support comprising an instrument carrier which is mounted on a linkage system rotatably supported about a column and constructed and arranged to provide for adjustment of the position of an instrument carried by the instrument carrier in said spatial envelope, characterised in that the instrument carrier comprises an elongated rod-like member extending through and secured to a ball of a ball joint arrangement a ball supporting member of which is mounted on said linkage system, in that counterbalancing means is adjustably mounted on the rod-like member at an end portion thereof remote from that at which the instrument is supported, and in that the ball joint arrangement has associated therewith clamping means which normally clamps the ball against rotation relatively to said ball supporting member but which may be caused to unclamp the ball on actuation of a switch (or like) device.

Preferably, in an adjustable stand as set out in the last preceding paragraph, said counterbalancing means comprises a weight and means for adjusting the position of the weight along three mutually perpendicular axes relatively to said rod-like member, one of said axes being parallel to the lengthwise direction of that member. Such an arrangement facilitates adjustment of the weight into a position in which the centre of gravity of the particular instrument(s) carried by the instrument carrier, the supporting parts and the counterbalancing means, coincides with the centre of the ball of the ball joint arrangement so as to avoid uncontrolled movement of the parts about the ball centre when the clamping means is unclamped. The counterbalancing means thus enables adjustments of the position of the centre of gravity of the components just above referred to to be made (for example, when one instrument is exchanged for another of different mass and configuration, or when an additional instrument is added to the instrument carrier) without the necessity for adjusting the position of the instrument(s) relatively to the carrier.

In an adjustable support as set out in the last preceding paragraph but one, the ball of said ball joint arrangement is preferably supported on an annular face of a ball-supporting member, and the clamping means comprises a brake ring which overlies the ball supporting member and has an inclined face which surrounds an upper portion of the ball and is urged into clamping engagement therewith under the action of spring means, a fluid pressure operated piston arrangement being arranged to act on an under side of the brake ring to overcome the action of the spring means on actuation of said switch device. The piston arrangement conveniently comprises an annular rubber U-ring type piston which is housed within an annular channel formed in an upper surface of the ball supporting member to which channel air under pressure may be admitted under the control of a valve arrangement actuated by said switch device.

One field in which an adjustable support in accordance with the invention is likely to be particularly useful is that of neurosurgery especially when delicate operations are to be performed on the brain. Sometimes such operations are performed with the patient lying on an operating table, in others the patient may be supported in a sitting position, particularly if the surgeon is tall. With a view to permitting observation of any part of the brain under these conditions it is desirable that the optical instrument is capable of spatial movement in an envelope in the form of a hemisphere about the head of a patient, and that this hemispherical envelope is capable of being described at a considerable range of vertical levels to take account, for example, of a wide range of heights of surgeons and other observers.

With a view to providing, as nearly as practicable, for the desired range of displacements of an optical instrument carried by an adjustable support as set out in the last preceding paragraph but three, preferably the linkage system on which the ball joint arrangement is mounted comprises a first carrier arm an outer end portion of which carries the ball supporting member and an inner end portion of which is pivotally supported for rotation about a first axis provided by a first joint arrangement which is supported by an outer end portion of a second supporting arm, an inner end portion of the second supporting arm being pivotally mounted, about a second axis arranged transversely to the first axis, by a second joint arrangement on a turret rotatably mounted about said column by means of a third joint arrangement providing a third axis parallel to the first axis. It will be appreciated that, with an arrangement as just described, heightwise movements of an instrument carried by the adjustable stand are effected as a consequence of pivotal movement of the second supporting arm about said second axis, while movements in a horizontal plane are effected as a consequence of pivotal movements of one or both of the first and second supporting arms about the first and third axes respectively.

With a view to avoiding undesired angular movements of an instrument carried by an adjustable support as set out in the last preceding paragraph but four and organised as set out in the last preceding paragraph, the second supporting arm preferably forms part of a parallel linkage arrangement which is arranged, during pivotal movement of the second supporting arm about said second axis, to maintain said first axis in an at least substantially vertical disposition.

While an adjustable support as set out in the last preceding paragraph but five and organised as set out in the last preceding paragraph but one may have said column supported by the floor or from the ceiling, preferably the column forms part of a trolley by which the support may be moved from one location to another, for which purpose conveniently the trolley is mounted on castors and is provided with supporting pads coupled with a trolley handle for moving the trolley in such manner that, when the handle is moved to one position, the supporting pads are lowered to engage the floor and take the weight of the support, while, when the handle is moved to a second position, the pads are raised to permit movement of the trolley on the castors by pulling or pushing the handle.

In view of the fact that, as mentioned in the opening paragraph of this specification, it is often desirable to utilise a plurality of optical instruments simultaneously for various observations during a delicate surgical operation, an adjustable support as set out in the last preceding paragraph but six and organised as set out in the last preceding paragraph but two is preferably provided with second adjustable counterbalancing means for counterbalancing turning moments of the second supporting arm and parts supported thereby about said second axis, and, with a view to avoiding the need of having relatively heavy weights supported on an extension of said second supporting arm (with consequent danger of collision of such weights with other objects or persons involved in the operation when the position of the instrument(s) is moved, particularly about said second or third axes) preferably the second counterbalancing means comprises a tension spring housed within the column and connected at one end portion, by connecting means, for example a cable, to a member adjustable lengthwise of an extension of the second supporting arm which extends beyond the second axis, and, at the other end portion, to tension adjusting means by which the spring is anchored in the column. The use of such a spring arrangement also reduces quite materially (as compared with the use of counterbalancing weights) the inertia to be overcome in making adjustments to the position of the instrument(s) which involve pivotal movements about the said second and third axes.

With a view to maintaining an instrument carried by the instrument carrier in a desired position between successive adjustments, an adjustable support as set out in the last preceding paragraph but seven and organised as set out in the last preceding paragraph but three is preferably provided with clamping means associated with each of said first, second and third joint arrangements for restraining pivotal movement of a first joint member relatively to a second joint member, each of said clamping means being arranged to be unclamped by the admission of fluid under pressure to these clamping means under the control of a switch device operable when it is desired to adjust the position of an instrument supported by the support. Conveniently, each of the clamping means associated with the first, second and third joint arrangements comprises a tapered annular surface associated with one of the joint members and a brake ring associated with the other one of the joint members and having a tapered surface movable into wedging engagement with that on the first mentioned joint member under the action of spring means and the admission of fluid under pressure to the clamping means causes a piston to act on the brake ring in opposition to spring means when it is desired to urge the brake ring out of clamping engagement. Furthermore, to facilitate adjustment both of orientation of the instrument(s) carried by the instrument carrier and of the spatial position of the instrument(s), it is convenient to arrange that each of the clamping means associated with the first, second and third joint arrangements is unclamped by the admission of air under pressure under the control of a valve arrangement which is actuatable by the switch device by which the clamping means associated with the ball joint arrangement for the instrument carrier is actuated. Such switch device may be mounted on a handle on the instrument carrier, or may be foot operated, or mouth operated.

From what has been said hereinbefore it will be appreciated that an adjustable support in accordance with the invention is likely to possess a number of advantages over supports currently available. For example, it may be pointed out that the ball joint arrangement of an adjustable support as set out in the last preceding paragraph but eight provides a relatively inexpensive, simple and compact arrangement, for permitting a substantially universal movement of the instrument carrier about a centre (provided by the centre of the ball) as compared, for example, with the triple axis linkage of the support disclosed in said UK patent specification No. 1357261 which necessitates a number of specially shaped component links which, together, occupy a considerable space around the observation point. Furthermore, with the ball joint arrangement only one clamping means is required to hold the carrier in its desired orientation instead of the three clamping (or blocking) devices required with the triple axis linkage of the support disclosed in the said specification. As for the clamping means referred to in the last preceding paragraph and in the last preceding paragraph but six respectively, it will be appreciated that they are of the "fail-safe" type so as to leave the various components clamped in the event of failure of the supply.

There will now be given, with reference to the accompanying drawings, a more detailed description of an adjustable support which is illustrative of the invention. It is, however, to be clearly understood that the illustrative support is selected for description by way of exemplification and not by way of limitation of the invention.

BRIEF DESCRIPTION OF THE DRAWINGS

In the accompanying drawings:

FIG. 1 is a general, somewhat schematic, view of the illustrative support, mainly in right hand side elevation, but with some parts broken away;

FIG. 2 is a side elevation view of first counterbalancing means and a ball joint arrangement for an instrument carrier;

FIG. 3 is a view, partly in front elevation and partly in section on the line III—III in FIG. 2;

FIG. 4 is a section on the line IV—IV in FIG. 2;

FIG. 5 is a section on the line V—V in FIG. 3;

FIG. 6 is a view showing, largely in section, a first joint arrangement by which a carrier supporting arm is pivoted on a second supporting arm;

FIG. 7 is a view of said first joint arrangement, chiefly in section on the line VII—VII in FIG. 6, showing also, from beneath, a portion of the first carrier supporting arm and the ball joint arrangement;

FIG. 8 is a detail view chiefly in section on the line VIII—VIII in FIG. 6;

FIG. 9 is a view partly in section on the line IX—IX in FIG. 7;

FIG. 10 is a view, in side elevation with some parts broken away, showing a second joint arrangement between the second carrier supporting arm, a tie rod, and a turret head;

FIG. 12 is a view, partly in elevation and partly in section on the line XII—XII in FIG. 1 and looking in the direction of the arrows, of a third joint arrangement, and clamping means associated therewith, by which the turret head is rotatably mounted on a column of a trolley of the illustrative support.

BEST MODE OF CARRYING OUT THE INVENTION

Figure 11:
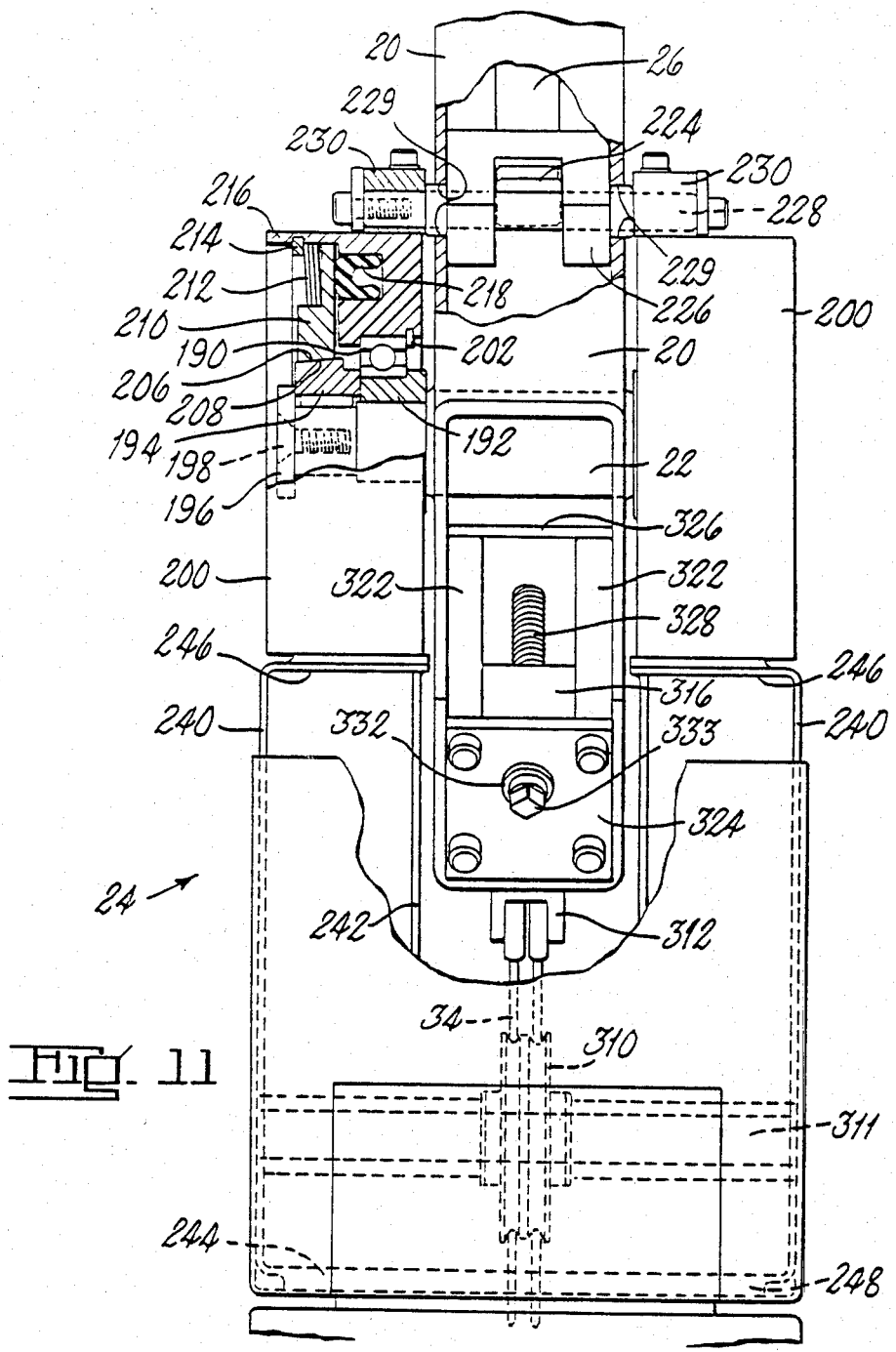
FIG. 11 is a view, chiefly in end elevation, but partly in section on the line XI—XI in FIG. 10, of the second joint arrangement and associated parts.

The illustrative stand is arranged to support an optical instrument, such as a binocular microscope suitable for use as an aid to surgery, in such manner that the optical instrument may be readily moved, by a surgeon performing a surgical operation, from one position to another within a desired envelope, and/or adjusted to direct its optical axis in a desired orientation, and may then be clamped in the desired position/orientation without the expenditure of any great effort.

With these and other objectives (to be mentioned hereinafter) in mind, the optical instrument such as a binocular microscope M (FIG. 1) is attached, in any convenient manner, to a lower end portion of an elongated rod-like carrier, conveniently provided by a shaft 10, which extends through a ball 12 (and is rigidly secured thereto) of a ball joint arrangement 14, a ball supporting member of which is mounted on a linkage system rotatably supported on a column 30. The linkage system is constructed and arranged (as will be hereinafter described) to provide for adjustment of the position of an instrument carried by the instrument carrier in the desired spatial envelope. The ball joint arrangement facilitates adjustment of the orientation of the instrument carried by the instrument carrier at any given position within the spatial envelope just referred to. The linkage system supporting the ball joint arrangement comprises a first carrier supporting arm 16 on an outer end portion of which said ball supporting member is carried and which is pivotally supported, at its inner end portion, for rotation about a first axis A which is provided by a first joint arrangement 18 which is supported by an outer end portion of a second supporting arm 20. An inner end portion of the arm 20 is pivotally mounted for movement about a shaft 22 of a second joint arrangement 23 mounted, as hereinafter described, in a turret 24, the shaft 22 providing a second axis B, which is arranged transversely with respect to the first axis A but considerably displaced therefrom. As will be seen from FIG. 1 the second axis B is arranged to be horizontal so that the pivoting of the arm 20 about the shaft 22 provides for raising or lowering of the joint arrangement 18 and hence of the carrier 10 and apparatus supported thereby.

The arm 20, and the tie rod 26 arranged parallel with the arm 20, provide a parallel linkage arrangement which will be hereinafter described, the function of which is to maintain the first axis A in a vertical direction during heightwise movements of the joint arrangement 18, arm 16 and parts supported thereby. The turret 24 is itself mounted for pivotal movement about a third axis C of a third joint arrangement 28 supported by an upper end portion of the column 30, the axis C being also vertically disposed (as seen in FIG. 1). As will be hereinafter described, the column 30 forms part of a trolley 32 by which the stand can be readily moved from one location to another.

The illustrative stand also includes first counterbalancing means for counterbalancing the weight of the optical instrument about the ball 12 and second counterbalancing means for counterbalancing turning movements of the arm 20 and parts supported thereby about the axis B provided by the shaft 22. The first counterbalancing means comprises a weight W and means (hereinafter described) for mounting the weight on an upwardly extending portion of the carrier shaft 10 (i.e. at an end portion remote from that at which an instrument is supported) with provision for adjusting the position of the weight along three mutually perpendicular axes so that the centre of gravity of the optical instrument supported on the carrier shaft, the supporting parts and the first counterbalancing means can readily be adjusted to coincide with the centre of the ball 12 of the ball joint arrangement. This facility is desirable when instruments of different mass and configuration are supported by the carrier shaft 10. The second counterbalancing means comprises a tension spring 300 housed within the column 30 and connected, at an upper end portion, by means of a cable 34 to a block 36 adjustable lengthwise of a portion of the arm 20 which extends, to the right as shown in FIG. 1, beyond the shaft 22. A lower end portion of the spring is anchored in the column by means for adjusting the tension exerted by the spring.

Clamping means is provided (as will hereinafter be described) in association with the ball joint arrangement 14, and with each of the first, second and third joint arrangements, 18, 23 and 28 for retaining the optical instrument in a desired position and/or orientation, the clamping means being arranged to be unclamped by the application of pneumatic pressure under the control of a switch device operable by the surgeon when he desires to adjust the position and/or orientation of the optical instrument. A fail-safe arrangement is thus provided whereby in the event of failure of the electrical or pneumatic supply, the clamping means remains in the clamping position to prevent inadvertant movement of the stand or instrument(s) carried thereby.

The various portions of the illustrative stand will now be described in greater detail.

Fixedly secured, as by welding for example, to the upper end portion of the carrier shaft 10 is a locating sleeve 40 (see FIGS. 3 and 4) which is shaped to provide guiding surfaces extending axially of the shaft 10. As shown in FIG. 4 the locating sleeve 40 may conveniently be of hexagonal cross section providing six guide surfaces 42 on which is slidably fitted corresponding inner faces of a sleeve-like slide 44 an upper portion of which has a cylindrical outer surface 47 while a lower portion 45 is threaded to engage with an internally threaded adjusting sleeve 46 (see also FIG. 2). A disc 48 (FIG. 3) is secured to a lower end portion of the locating sleeve 40 and a shoulder 49 formed internally at lower end portion of the adjusting sleeve 46 rests on the disc 48, being retained thereagainst by a circlip 50. The adjusting sleeve is thereby restrained against axial movement with respect to the carrier shaft 10 but may be rotated therearound to move the adjusting slide 44 axially of the shaft, such movement being limited in an upwards direction (as viewed in FIG. 3) by engagement of the upper end of the portion 45 with a screw 52 extending through an upper end portion of the adjusting sleeve 46.

A block 54 has a depending stem portion which is received within and secured to an upper end portion of the adjusting slide 44 and an elongated box-like guide member 56 (see FIGS. 2 and 3) is clamped to the block 54 by a clamp 58 and screws 60. The lengthwise dimension of the guide member 56 extends perpendicularly to the axis of the carrier shaft 10. Slidably received on the guide member 56 is a carrier 62 which is secured, by a screw 64, to a block 66 (see also FIG. 5) slidably received within the guide member 56, the screw 64 extending through a slot 68 extending lengthwise of the guide member. A threaded rod 70 is rotatably mounted in bearing blocks 72, 74 secured within the guide member 56 (the rod being held against axial movement relatively to the block 74 by means of a flange 76 on the rod 70 and a washer and locknut arrangement 78) and has threaded engagement within a bore in the block 66. Rotation of the threaded rod 70, by means of a knob 80 on one end thereof, causes the block 66 to move lengthwise of the guide member 56 similarly to move the carrier 62. The block 54 (see FIGS. 2 and 3) is provided with grooves 55 to permit the passage of inwardly directed flange portions of the carrier 62 therepast. The carrier 62 has secured thereto a second elongated box-like guide member 82 the lengthwise dimension of which extends perpendicuarly to the plane containing the axes of guide member 56 and of the carrier shaft 10. The counterweight W is guided for movements lengthwise of the guide member 82 and is secured by a screw 84 (extending through a slot 85 in one wall of the guide member 82) to a block 86 slidably received within the guide member 82 and threaded onto a threaded rod 88 rotatably mounted in bearing blocks 90, 92 secured in opposite end portions of the guide member 82. Knobs 94 are provided at each end of the threaded rod for adjustment of the counterweight along the guide member 82.

The ball 12 of the optical instrument carrier 10 is supported upon an inclined annular face 104 of a ball supporting member 102 (as shown in FIG. 9). The member 102 is fixedly secured to an outer end portion of the first carrier-supporting arm 16 which is fabricated from sheet metal into an elongated hollow rectangular box-like form. The ball supporting member 102 is cut away to provide a shallow conical face 106 to permit the shaft 10, and hence an optical instrument supported thereon, to partake of a wide range of angular movement of adjustment. Associated with the ball joint arrangement is a clamping device comprising a brake ring 110 having an internal inclined surface 112 which surrounds an upper portion of the ball 12 and is arranged to engage the ball surface with a wedging action firmly to clamp the ball and parts supported thereby in any desired position relatively to the ball supporting member 102, for which purpose an upper recessed surface 114 of the ring 110 is acted upon by a series of disc springs 116. A key 118, received in recesses in the ring 110 and in a peripheral upstanding wall 120 of the ball supporting member 102, holds the ring 110 against rotation. The springs 116 are retained in place by a locking ring 122 comprising an internal circlip received in an annular groove in the wall 120. The clamping device is unclamped to permit movement of the ball 12 by the action of pressurised fluid (in this case compressed air) on an annular rubber U-ring type piston 124 housed within an annular channel 126 formed in an upper surface of the ball supporting member 102 just below an underface of the brake ring 110. Air under pressure may be admitted via an inlet passage 128 which extends through the member 102 and opens into the channel 126 beneath the U-shaped cavity in the piston 124 to cause the piston to raise the brake ring against the action of the springs 116. A flexible protective rubber cover 130 seals the upper side of the ball joint arrangement. A flexible hose 132 supplies compressed air (under the control of a valve arrangement hereinafter referred to) to the inlet passage 128 when desired.

An inner end portion of the carrier arm 16 is reinforced at 109 (FIG. 6) and is secured (as by welding) to a lower end portion of a hollow shaft 134 forming part of the first joint arrangement 18. Lower and upper ball bearings 136, 138 surround the shaft and are spaced apart by a spacing sleeve 140. A retaining ring 142 holds the ball races in place upon the shaft as shown in FIG. 6. The ball bearings 136, 138 are respectively seated against shoulders 147 and 149 formed in an internal wall of a sleevelike bearing housing 144, lower and upper end portions of which are secured, conveniently by welding, to lower and upper end plates 146 and 148. Bridging the end plates and securely fixed thereto is a face plate 150 provided with a pair of flanges 151 which extend lengthwise of the bearing housing and to the right as viewed in FIGS. 6 and 7. By these flanges the first joint arrangement is pivotally connected with outer end portions of the supporting arm 20 and the tie rod 26. The bearing arrangement just described permits free pivotal movement of the first carrier supporting arm 16 relatively to the bearing housing 144 but restrains it against heightwise (axial) movement relatively thereto.

To clamp the shaft 134 against pivotal movement relatively to the housing 144 at all times except when it is desired to free it for adjustment of the position of the optical instrument supported by the carrier arm 16, a clamping device is provided. This clamping device comprises a base member 152 which is secured, by screws 153, to the upper end plate 148 of the bearing housing and surrounds an upper end portion of the shaft 134 which is provided with an external tapered surface 154 extending upwardly beyond an upper surface of the base member 152 over which extends a brake ring 156. The brake ring has a tapered bore providing an internal inclined surface 158, the inclination of which corresponds to that of the surface 154 of the shaft 134. A series of disc springs 160 act on an upper face of the brake ring 156 and are retained in position by a locking ring 162 received in an annular groove in a wall portion 164 of the base member 152, the thrust of the springs being effective to urge the brake ring into clamping engagement with the surface 154 of the shaft 134. The brake ring 156 is restrained against rotation relatively to the base member 152 by means of a key (not shown). The clamping device just described is unclamped by the action of compressed air (supplied via an inlet passage 165 from a hose 163) on an annular rubber piston 166 housed in an annular channel 168 formed in the upper face of the base member 152, the action being generally similar to that of the clamping device associated with the ball 12 of the carrier 10 hereinbefore described. A cover 170 (conveniently of sheet metal or plastic) is provided for the joint arrangement just above described.

Rotatably mounted in bush bearings provided in bearing housings 172 (FIG. 7) secured (e.g. by welding) in aligned bores in the flanges 151 is a lower pivot pin 174 which is pinned in a sleeve 176 which extends between, and is secured to, opposite side walls of the second supporting arm 20. The outer end portion of the tie rod 26 is provided with a part spherical rod end bearing 178 (FIGS. 6 and 8) through which extends an upper pivot pin 180, the inner member of the bearing 178 being located between two spacing sleeves 182 surrounding the pin 180. The pin 180 is housed in aligned bores in the flanges 151 and secured in place by screws 184 and associated washers.

The second carrier supporting arm 20 is rigidly secured to the shaft 22 of the second joint arrangement 23 (see FIG. 11), the shaft extending from both sides of the box-like structure forming the arm 20 into bearings 190 and associated clamping devices, one of which is shown, partly in section, in FIG. 11. The other is like it but a mirror image thereof. An inner race of each bearing 190 is clamped between a shoulder on a bearing spacer 192 and an inner face on a lock wedge member 194 which is keyed to an outer end portion of the shaft 22. A washer 196 secured against the end of the shaft by a screw 198 (see also FIG. 10) clamps the parts 194 and 192 together against a shoulder formed on the shaft 22 (see FIG. 11). The other race of each bearing 190 is received in a central bore in a bearing housing block 200, and is retained therein by a circlip 202 and a shoulder formed in said bore.

The two blocks 200 are secured on the turret 24 by means of screws 204. Each lock wedge member 194 has an inclined circumferencial face 206 on which rides a correspondingly inclined face 208 of a brake ring 210. As in the clamping devices above described, the brake ring 210 is held against rotation relatively to the block 200 by means of a key (not shown) and is urged in a direction to effect clamping of the shaft 22 (as a consequence of the wedging action of the faces 206, 208) by a series of spring discs 212 retained in place by a circlip 214 (see also FIG. 10) received within an annular groove in a wall portion 216 (FIG. 11) of the block 200. An annular rubber piston 218 housed in an annular channel 220 in the block 200 is provided for moving the brake ring 210 against the action of the springs 212 when compressed air is admitted to the channel 220 through a passage (not shown) when it is desired to unclamp the shaft 22.

An inner end portion of the tie rod 26 is secured, by means of a bolt 224 (FIG. 11), to a forked member 226 pivotally mounted on a pivot pin 228 opposite end portions of which extend through arcuate slots 229 in walls of the arm 20 and are secured in blocks 230 supported by the bearing housing blocks 200. The slots 229 are concentric with the axis of the shaft 22. The axes of the pivot pins 174, 180 (FIG. 6) and the pivot pin 228 and shaft 22 (FIG. 11) are all parallel and are so spaced that the arm 20, link 26 and their anchorages provide a parallel linkage system, as above mentioned, which is arranged to maintain the axis of the shaft 134 (FIG. 6) vertical during heightwise movements of the optical instrument carrier 10, so that the orientation of the optical instrument supported by the carrier shaft 10 does not change during such heightwise movement.

The turret 24 is fabricated from sheet metal and comprises spaced parallel outer walls 240 and inner walls 242 (FIG. 11) which are connected together by a base portion 244 and two top members 246. The bearing housing blocks 200 are carried by the top members 246, while the base portion 244 is secured (as by welding) to a plate 248 which is, in turn, secured to a flange 250 (FIG. 12) of a hollow shaft 252 the axis of which is disposed vertically and is part of the third joint arrangement 28 by which the turret is rotatably mounted on the column 30 of the trolley 32. The shaft 252 is rotatably mounted in ball bearings 254, 256 supported in a bearing housing sleeve 258 having upper and lower flange members 260, 262. Circlips 264, 266 retain the bearings in place in the bearing housing while a circlip 268 received in an annular groove in the shaft 252 engages the lower ball bearing 256 to restrain the shaft against axial movement. The upper flange member 260 is received within an upper end portion of the column 30 and is secured thereto by a clamping ring 270, the column 30 being hollow and fabricated from sheet metal. The lower flange member 262 is secured to a base member 272 which surrounds a lower end portion of the shaft 252 and forms part of a clamping device for holding the shaft against rotation. The base member 272 is provided with downwardly extending lugs 274 which are secured, by brackets 276, to wall portions of the column 30. The clamping device for the shaft 252 is generally similar to those above described and comprises a brake ring 278 having an internal tapered surface 280 co-acting with a similar tapered surface 282 formed on the shaft 252. Spring discs 284, supported by a circlip 286, urge the brake ring upwardly to clamp the shaft 252 against rotation, and a rubber ring piston 288 housed in an annular channel 290 in the base member 272 is acted upon by compressed air supplied to the channel 290 (through a passage, not shown) when it is desired to unclamp the shaft for rotation relatively to the column 30.

The second counterbalancing means for counterbalancing the turning movements of the arm 20 and parts carried thereby about the axis of the shaft 22 comprises a tension spring 300 (FIG. 1) housed within the column 30 and anchored, at a lower end portion, to spring tension adjusting means comprising a collar 302 threaded onto a threaded rod 304 rotatably mounted in a plate 306 secured in the column 30. An upper end portion of the spring 300 is connected to a double cable 34 which extends through the hollow shaft 252 of the turret and passes over a pulley 310 rotatably mounted on a cross-shaft 311 in the turret (see FIG. 11). An upper end portion of the cable 34 (see FIG. 10) is connected, by a link 312 and a pivot pin 314, to a lug 316 depending frm the block 36 which is slidably mounted between guide bars 320 and 322 secured to end plates 324 and 326 which guide bars extend parallel to the lengthwise dimension of the arm 20 and are secured by screws 323 to a right hand end portion of the arm as seen in FIG. 10. The block 36 is threaded on to a threaded rod 328 extending parallel to the guide bars 320 and 322 and rotatably mounted in the end plates 324 and 326 and held against axial movement by a circlip 330 and and a collar 332 adjacent a head portion 333 of the screwed rod by which it may be rotated to adjust the block 36 along the arm 20. The arrangement just above described provides a coarse adjustment of the counterbalancing action of the spring 300 (by rotation of the threaded rod 304 of the tension adjusting means, see FIG. 1) and a fine adjustment (by means of the threaded rod 328, see FIG. 10). Conveniently, the tension adjusting means is set with the block 36 at the mid point of its travel and an instrument of average mass supported by the carrier shaft 10. When the instrument is changed for one of a different mass (or when an additional instrument is added or removed) the change in mass may usually be counterbalanced merely by adjustment of the fine adjustment on rotation of the threaded rod 328 to re-adjust the position of the block 36.

A base portion of the trolley 32 may conveniently be formed to house any necessary electrical components such as transformers, rectifiers, relays and the like to provide low voltage supplies for lighting or other equipment with the optical instrument in use or for other purposes. Outlet sockets and switches may be provided for example on a panel (not shown) beneath the arm 16. The base portion of the trolley may also conveniently house any necessary valve arrangements associated with control equipment for the clamping devices, and connections whereby the stand may be connected to a "mains" supply of electricity and compressed air. Cables and hoses within the stand pass from the trolley base portion up the inside of the column 30, through the hollow shaft 252 of the turret and thence through a ducting 334 (FIGS. 6 and 10) within the arm 20, through a grommet 336 in the cover 170 (FIG. 6), via the hollow shaft 134 and thence, through an aperture 338 therein, into the hollow arm 16.

As indicated in FIG. 1, the trolley is provided with castors 340 and is preferably provided with supporting pads (not shown) which are coupled in well known manner, with a trolley handle (not shown) so that, when the handle is raised, the supporting pads are lowered to engage the floor and take the weight of the stand, while, when the handle is lowered, the pads are raised to permit movement of the trolley on the castors 340 by pulling or pushing the handle. The base portion of the trolley may be weighted as necessary to ensure the desired stability when the carrier arms 16 and 20 are in positions giving maximum reach of the microscope or other optical instrument(s) mounted on the carrier 10. The provision of a handle arrangement for moving the trolley as just described avoids the need for moving the stand by the application of force to upper portions of the column or turret and thus tends to avoid instability problems such as are found with certain known stands.

The supply of compressed air to the various clamping devices is conveniently controlled by a single valve arrangement situated in the base of the trolley-for example an electromagnetic valve arrangement operated by a switch device (not shown) which may be conveniently located on a handle 350 associated with the carrier 10 by which handle the position and/or orientation of the optical instrument supported by the carrier 10 may be adjusted. Alternatively the switch device may be a foot operated switch or a mouth operated switch suspended on the carrier 10. Thus only one switch device is required to unclamp simultaneously all the clamping devices.

A sensing device (not shown) associated with the second counterbalancing means is so organised that, in the event of loss of tension (e.g. by breakage of a part) in the system comprising the spring 300 and parts by which it is connected to the column 30 or the extension of the arm 20, the supply of compressed air is dumped so that, despite actuation of the switch device just above referred to, the various clamping devices remain clamped (or move to clamping position if the switch device is in its actuated position at the time the loss in tension occurs).

We claim:

1. An adjustable support for an optical or other instrument (M) including a linkage system (16,20) rotatably supported about a column (30), which linkage system permits adjustment of the position of the instrument in a predetermined spatial envelope, and means comprising a ball joint arrangement, comprising a ball (12) and a ball-supporting member (102), for carrying the instrument on a free end portion of said linkage system (16,20) remote from said column (30), which instrument-carrying means permits adjustment of the orientation of the instrument at any given position within said spatial envelope, clamping means (110) which normally clamps the ball (12) against rotation relatively to the ball-supporting member (102) but which may be caused to unclamp the ball on actuation of a switch (or like) device, and means (300) for counterbalancing the linkage system (16,20) about a horizontal pivot (22) in the vicinity of the column (30), characterized in that the instrument-carrying means comprises:

a rod-like member (10) extending through and secured to said ball (12) of said ball joint arrangement (14), one end portion of said rod-like member being arranged to have said instrument (M) mounted thereon and the other end portion of the rod-like member having adjustable counter-balancing means (W) mounted thereon, which counterbalancing means is adjustable to counterbalance the weight of the instrument carried by the rod-like member (10) about the center of the ball joint arrangement (14).

2. An adjustable support in accordance with claim 1 characterised in that said counterbalancing means mounted on the rod-like member (10) comprises a weight (W) and means (46, 80, 94) for adjusting the position of the weight along three mutually perpendicular axes relatively to said rod-like member (10), one of said axes being parallel to the lengthwise direction of that member.

3. An adjustable support in accordance with claim 1 characterised in that the ball (12) of said ball joint arrangement is supported upon an annular face (104) of ball supporting member (102), and wherein the clamping means comprises a brake ring (110) which overlies the ball supporting member (102) and has an inclined face (112) which surrounds an upper portion of the ball and is urged into clamping engagement therewith under the action of spring means (116), a fluid pressure operated piston arrangement (124) being arranged to act on an under side of the brake ring (110) to overcome the action of the spring means on actuation of said switch device.

4. An adjustable support in accordance with claim 3 characterised in that the piston arrangement comprises an annular rubber U-ring type piston (124) which is housed within an annular channel (126) formed in an upper surface of the ball supporting member (102) to which channel air under pressure may be admitted under the control of a valve arrangement actuatable by said switch device.

5. An adjustable support in accordance with claim 1 characterised in that the linkage system on which the ball joint arrangement is mounted comprises a first carrier arm (16) an outer end portion of which carries the ball supporting member and an inner end portion of which is pivotally supported for rotation about a first axis (A) provided by a first joint arrangement (18) which is supported by an outer end portion of a second supporting arm (20), an inner end portion of the second supporting arm being pivotally mounted, about a second axis (B) arranged transversely to the first axis, by a second joint arrangement (23) on a turret (24) rotatably mounted about said column (30) by means of a third joint arrangement (28) providing a third axis (C) parallel to the first axis.

6. An adjustable support in accordance with claim 5 characterised in that the second supporting arm (20) forms part of a parallel linkage arrangement (20, 26) which is arranged, during pivotal movement of the second supporting arm about said second axis (B), to maintain said first axis (A) in an at least substantially vertical disposition.

7. An adjustable support in accordance with claim 6 characterised in that the column (30) forms part of a trolley (32) by which the support may be moved from one location to another.

8. An adjustable support in accordance with claims 5 or 6 characterised in that the counterbalancing means (300) is provided for counterbalancing turning moments of the second supporting arm (20) and parts supported thereby about said second axis (B), counterbalancing means comprising a tension spring (300) housed within the column (30) and connected at one end portion, by connecting means, for example a cable (34), to a member (36) adjustable lengthwise of an extension of the second supporting arm (20) which extends beyond the second axis (B), and, at the other end portion, to tension adjusting means (302, 304) by which the spring is anchored in the column.

9. An adjustable support in accordance with claim 5 characterised in that there is associated with each of the first, second and third joint arrangements (18, 23, 28) a clamping means (156, 210, 278) for restraining pivotal movement of a first joint member relatively to a second joint member, each of said clamping means being arranged to be unclamped by the admission of fluid under pressure to these clamping means under the control of a switch device operable when it is desired to adjust the position of an instrument supported by the support.

10. An adjustable support in accordance with claim 9 characterised in that each of the clamping means associated with the first, second and third joint arrangements comprises a tapered annular surface (154, 206, 282) associated with one of the joint members and a brake ring (156, 210, 278) associated with the other one of the joint members and having a tapered surface (158, 208, 280) movable into wedging engagement with that on the first mentioed joint member under the action of spring means (160, 212, 284) and wherein the admission of fluid under pressure to the clamping means causes a piston (166, 218, 288) to act on the brake ring in opposition to the spring means when it is desired to urge the brake disc out of clamping engagement.

11. An adjustable support in accordance with either one of claims 9 and 10 characterised in that each of said clamping means associated with the first, second and third joint arrangements is unclamped by the admission of air under pressure under the control of a valve arrangement which is actuatable by the switch device by which the clamping means associated with the ball joint arrangement for the instrument carrier is actuated.

* * * * *